United States Patent
Okuda (10) Patent No.: US 9,427,209 B2
(45) Date of Patent: Aug. 30, 2016

(54) ULTRASOUND PROBE, ULTRASOUND DIAGNOSTIC IMAGING APPARATUS AND MANUFACTURING METHOD OF ULTRASOUND PROBE

(71) Applicant: KONICA MINOLTA, INC., Chiyoda-ku, Tokyo (JP)

(72) Inventor: Shuhei Okuda, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 142 days.

(21) Appl. No.: 14/167,504

(22) Filed: Jan. 29, 2014

(65) Prior Publication Data

US 2014/0221841 A1 Aug. 7, 2014

(30) Foreign Application Priority Data

Jan. 31, 2013 (JP) .................. 2013-016800

(51) Int. Cl.
*A61B 8/14* (2006.01)
*A61B 8/00* (2006.01)
*B06B 1/06* (2006.01)

(52) U.S. Cl.
CPC ............ *A61B 8/4444* (2013.01); *B06B 1/0622* (2013.01); *B06B 1/0677* (2013.01); *A61B 8/4405* (2013.01); *A61B 8/4483* (2013.01)

(58) Field of Classification Search
USPC ....................................................... 600/459
See application file for complete search history.

(56) References Cited

U.S. PATENT DOCUMENTS

| 6,298,726 B1 * | 10/2001 | Adachi ................... A61B 8/08 367/140 |
| 2008/0252172 A1 | 10/2008 | Yetter et al. |
| 2009/0069689 A1 | 3/2009 | Isono |
| 2010/0231095 A1* | 9/2010 | Kubota ................... C04B 35/01 310/357 |
| 2012/0310091 A1 | 12/2012 | Ohnuma et al. |

FOREIGN PATENT DOCUMENTS

| JP | 2009-061112 A | 3/2009 |
| JP | 2012245307 A | 12/2012 |
| WO | 2011064934 A1 | 6/2011 |

OTHER PUBLICATIONS

Japanese Office Action (and English translation thereof) dated Feb. 2, 2016, issued in counterpart Japanese Application No. 2013-016800.

* cited by examiner

*Primary Examiner* — Joel F Brutus
(74) *Attorney, Agent, or Firm* — Holtz, Holtz & Volek PC

(57) ABSTRACT

Disclosed is an ultrasound probe which outputs ultrasound on a basis of a drive signal which is to be received. The ultrasound probe including a composite piezoelectric layer in which a piezoelectric material and a polymer material are arranged alternately in a one-dimensional array or in a two-dimensional array, an acoustic reflection layer which has an acoustic impedance higher than an acoustic impedance of the composite piezoelectric layer and an adhesion layer which bonds the composite piezoelectric layer and the acoustic reflection layer wherein in a bonding surface of the composite piezoelectric layer that bonds with the acoustic reflection layer, a polymer material part is concaved in a direction opposite to an acoustic reflection layer side comparing to an piezoelectric material part.

12 Claims, 8 Drawing Sheets

ULTRASOUND PROBE, ULTRASOUND DIAGNOSTIC IMAGING APPARATUS AND MANUFACTURING METHOD OF ULTRASOUND PROBE

BACKGROUND OF THE INVENTION

1. Field of the Invention

The present invention relates to an ultrasound probe which includes a composite piezoelectric layer which realizes high sensitivity and wider bandwidth, an ultrasound diagnostic imaging apparatus and a manufacturing method of the ultrasound probe.

2. Description of Related Art

Ultrasound diagnostic imaging apparatuses of high image quality are desired, and making ultrasound probes realize high sensitivity and wider bandwidth is suggested as a method for realizing high image quality.

An ultrasound probe makes an piezoelectric material excite elastic vibration whose thickness corresponds to ¼) and emits ultrasound generated by the elastic vibration to a subject. With respect to the ultrasound energy emitted in the direction opposite to the direction in which a subject is positioned, since the ultrasound is reflected in the direction opposite to the direction toward a subject by an acoustic reflection layer having high acoustic impedance, which is disposed on the side opposite to the side of the subject, the ultrasound energy to be emitted is increased and high sensitivity can be realized.

Further, a composite piezoelectric layer is used as a member for generating ultrasound. A composite piezoelectric layer is formed of a piezoelectric material such as lead zirconate (PZT) and a polymer material such as resin wherein the materials are arranged alternately in the direction orthogonal to the direction toward a subject who is to be emitted and the materials are integrated. The composite piezoelectric layer is made to have low acoustic impedance by being provided with a polymer material and is made to have acoustic impedance close to that of a subject which is low comparing to the acoustic impedance of the piezoelectric material. Thereby, high sensitivity and wider bandwidth can be realized.

Figure 11:
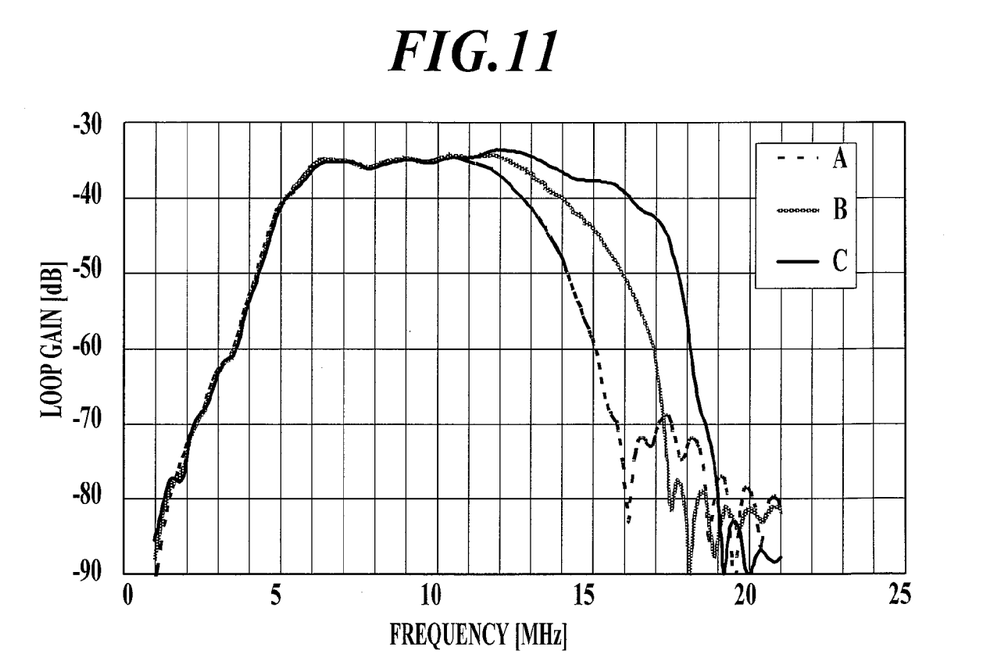
FIG. 11 shows a relation between thickness of an adhesive layer and a band to be irradiated.

However, taking the above measures is not enough to realize high sensitivity and wider bandwidth. FIG. 11 shows that the thickness of an adhesion layer between the piezoelectric material and the acoustic reflection layer has relevance with the frequency band width. The horizontal axis shows frequency (MHz) and the vertical axis shows response sensitivity (Loop Gain) of piezoelectric material with respect to frequency in decibel (dB). The curve A shows the case where the thickness of the adhesion layer between the piezoelectric material alone and the acoustic reflection layer is 1.5 µm, the curve B shows the case where the above thickness is 1.0 µm and the curve C shows the case where the above thickness is 0.5 µm. As it is clear from the curves, as the thickness of the adhesion layer that attaches the piezoelectric material and the acoustic reflection layer is thinner, the frequency band at the desired response sensitivity of the piezoelectric material is wider. Therefore, in a composite piezoelectric layer in which a piezoelectric material and a polymer material are arranged alternately in the direction orthogonal to the direction toward a subject to be irradiated, the frequency band also becomes wider if the thickness of the adhesion layer which attaches the piezoelectric material parts in the composite piezoelectric, layer and the acoustic reflection layer becomes thinner. That is, making the thickness of the adhesion layer which attaches the piezoelectric material parts in the composite piezoelectric layer and the acoustic reflection layer thinner is important in order to realize even wider bandwidth.

In order to realize this, the adhesion layer between the piezoelectric material parts in the composite piezoelectric layer and the acoustic reflection layer needs to be made thin by performing the bonding by the adhesion layer after performing mirror polishing on the bonding surfaces of the composite piezoelectric layer, which is to be bonded with the acoustic layer by the adhesion layer, and smoothen the bonding surfaces before the bonding.

However, because the hardness of the piezoelectric material such as PZT which forms the piezoelectric material and the hardness of the polymer material formed of a resin differ from each other, when mirror polishing is to be performed on the bonding surface of the composite piezoelectric layer, the piezoelectric material will be polished more comparing to the polymer material. As a result, the bonding surface of the piezoelectric material and the polymer material will be bumpy and the piezoelectric material parts cannot be smoothened sufficiently causing a problem that the thickness of the adhesion layer cannot be uniformly and sufficiently thin.

In view of such problem, JP 2009-61112 discloses a technique for manufacturing a composite piezoelectric layer by cutting out the piezoelectric material to their midpoint and not all the way to the bottom and filling the polymer material in the spaces formed by cutting out the piezoelectric material. It is described that because the entire bonding surface that bonds with the acoustic reflection layer is the piezoelectric material in the composite piezoelectric layer formed by the above method, bumps due to difference in hardness between the piezoelectric material and the polymer material does not occur even if mirror polishing is performed; and thus, the adhesion layer can be thin.

SUMMARY OF THE INVENTION

However, in the technique described in JP 2009-61112, there is a problem that the advantageous effect as a composite piezoelectric layer is reduced because the piezoelectric material is not cut out to the bonding surface with the acoustic reflection layer. Therefore, in order to improve the advantageous effect, it is necessary to cut out the piezoelectric material at the parts where the material needs to be cut out to the extent almost reaching the bonding surface with the acoustic reflection layer. Therefore, cracks can easily occur in the bonding surface and there are problems in maintaining durability and stability of the composite piezoelectric layer; thus, desired ultrasound cannot be generated stably.

The present invention is made in view of the above problems and an object of the present invention is to provide an ultrasound probe provided with a composite piezoelectric layer which realizes high sensitivity and wider bandwidth and which has high durability and stability, an ultrasound diagnostic imaging apparatus and a manufacturing method of the ultrasound probe.

To realize the above object, according to a first aspect of the present invention, an ultrasound probe outputs ultrasound on a basis of a drive signal which is to be received, and the ultrasound probe includes a composite piezoelectric layer in which a piezoelectric material and a polymer material are arranged alternately in a one-dimensional array or in a two-dimensional array, an acoustic reflection layer which has an acoustic impedance higher than an acoustic impedance of the composite piezoelectric layer and an adhesion layer which bonds the composite piezoelectric layer and the acoustic reflection layer, and in a bonding surface of the composite piezoelectric layer that bonds with the acoustic reflection layer, a polymer material part is concaved in a direction opposite to an acoustic reflection layer side comparing to an piezoelectric material part.

Preferably, a thickness t (μm) of the adhesion layer between a bonding surface of the piezoelectric material part of the composite piezoelectric layer and the acoustic reflection layer is $0 < t \leq 1.0$.

Preferably, a surface roughness Ra (μ) of a surface of the piezoelectric material in the composite piezoelectric layer opposite to the acoustic reflection layer side is $Ra \leq 0.4$.

To realize the above object, according to a second aspect of the present invention, an ultrasound diagnostic imaging apparatus includes an ultrasound probe, a transmission unit which generates the drive signal and an image generation unit which generates ultrasound image data for displaying an ultrasound image on a basis of the received signal output by the ultrasound probe.

Preferably, the drive signal is a rectangular wave including a plurality of pulses, a pulse width of at least one pulse among the plurality of pules being different from pulse widths of other pulses.

Preferably, the drive signal includes a first pulse signal, a second pulse signal whose polarity is different from the first pulse signal and a third pulse signal whose polarity is same as the first pulse signal, and a pulse width of the first pulse signal, the pulse width of the second pulse signal and the pulse width of the third pulse signal are different from one another.

To realize the above object, according to a third aspect of the present invention, a manufacturing method of an ultrasound probe which outputs ultrasound on a basis of a drive signal which is to be received, the ultrasound probe comprising a composite piezoelectric layer in which a piezoelectric material and a polymer material are arranged alternately in a one-dimensional array or in a two-dimensional array and an acoustic reflection layer which has an acoustic impedance higher than an acoustic impedance of the composite piezoelectric layer and the composite piezoelectric layer and the acoustic reflection layer being bonded by an adhesion layer, the manufacturing method includes forming the composite piezoelectric layer in which the piezoelectric material and the polymer material are arranged alternately, removing parts of polymer material parts in a bonding surface of the composite piezoelectric layer which bonds with the acoustic reflection layer so that the polymer material parts concave in a direction opposite to an acoustic reflection layer side comparing to piezoelectric material parts, polishing a bonding surface of the composite piezoelectric layer after the removing and bonding of the bonding surface of the composite piezoelectric layer and the acoustic reflection layer by the adhesion layer.

Preferably, removing of the parts of the polymer material parts in the removing is performed by etching.

Preferably, removing of the parts of the polymer material parts in the removing is performed by dicing.

To realize the above object, according to a fourth aspect of the present invention, a manufacturing method of an ultrasound probe which outputs ultrasound on a basis of a drive signal which is to be received, the ultrasound probe comprising a composite piezoelectric layer in which a piezoelectric material and a polymer material are arranged alternately in a one-dimensional array or in a two-dimensional array and an acoustic reflection layer which has an acoustic impedance higher than an acoustic impedance of the composite piezoelectric layer and the composite piezoelectric layer and the acoustic reflection layer being bonded by an adhesion layer, the manufacturing method includes filling the polymer material in spaces formed in the piezoelectric material with a predetermined interval therebetween to form the composite piezoelectric layer, polishing the bonding surface of the composite piezoelectric layer after the filling, and bonding of the bonding surface of the composite piezoelectric layer and the acoustic reflection layer by the adhesion layer, and in the filling, the polymer material is filled so that a polymer material part in the bonding surface of the composite piezoelectric layer that bonds with the acoustic reflection layer is concaved in a direction opposite to an acoustic reflection layer side comparing to an piezoelectric material part.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an ultrasound probe 1 and an ultrasound diagnostic imaging apparatus 2 according to the present invention will be described with reference to the drawings.

Figure 1:
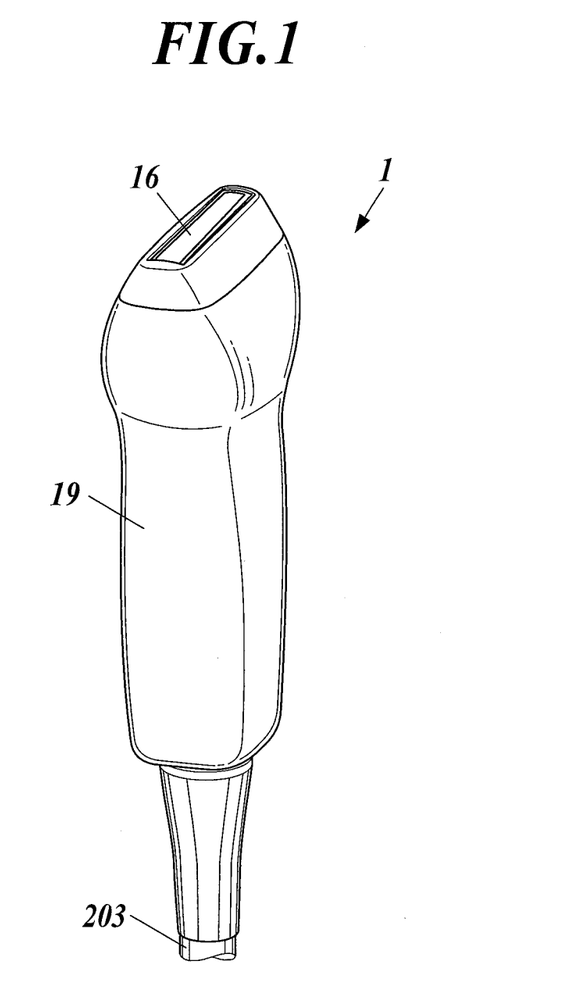
FIG. 1 shows an outer configuration of an ultrasound probe.

FIG. 1 shows an outer configuration of the ultrasound probe 1 according to the embodiment. The ultrasound probe includes an acoustic lens 16 which makes direct contact with a subject, a case holding unit 19 and a cable 203.

Figure 2A:
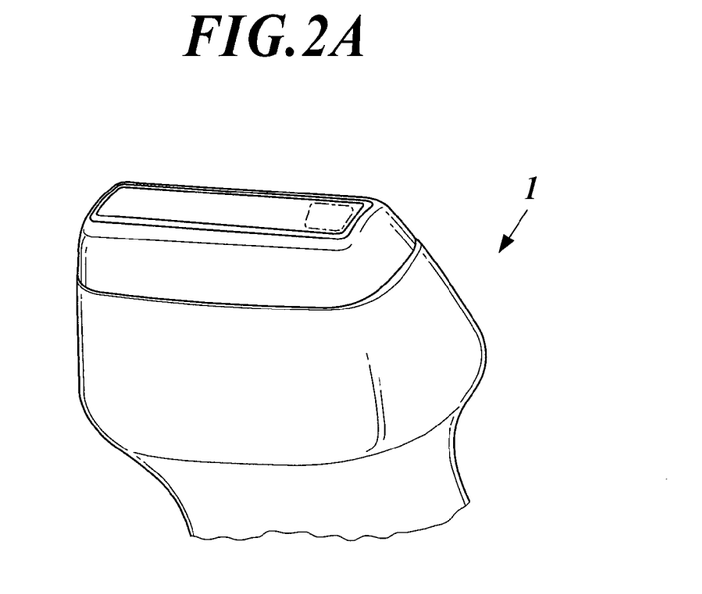
FIG. 2A shows an outline of the ultrasound probe.
Figure 2B:
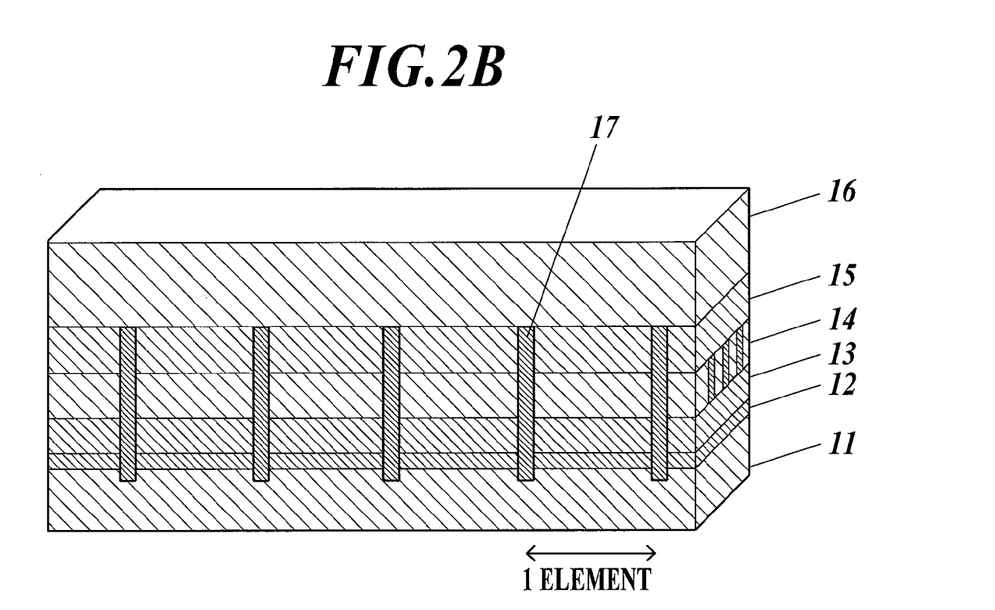
FIG. 2B shows an outline of the ultrasound probe.

FIG. 2A shows a part of the outer configuration of the ultrasound probe 1. FIG. 2B is a schematic sectional view of the portion indicated by dot-dash-line in the ultrasound probe 1 shown in FIG. 2A. The ultrasound probe 1 of the embodiment includes, layered from the bottom, a backing layer 11, a flexible printed board 12, an acoustic reflection layer 13, a composite piezoelectric layer 14 which is configured of a piezoelectric material 14a and a polymer material 14b being integrated, an acoustic matching layer 15 and an acoustic lens 16, and the layers are joined to each other by adhesion layers.

The composite piezoelectric layer 14 is a layer formed of a piezoelectric material and a polymer material such as epoxy resin being arranged alternately in the direction orthogonal to the direction in which the composite piezoelectric layer 14 emits ultrasound toward a subject, the piezoelectric material and the polymer material being integrated. Because the piezoelectric material 14a and the polymer material 14b are integrated, the composite piezoelectric layer has about the same electromechanical coupling factor as that of the piezoelectric material 14a and on the other hand, has acoustic impedance lower comparing to that of the piezoelectric material 14a. In such way, difference in acoustic impedance between the composite piezoelectric layer 14 and the acoustic matching layer 15 is made to be small while the resonant frequency characteristic having broad frequency band.

Here, the acoustic impedance of the composite piezoelectric layer can be obtained by using the volumes of the piezoelectric material and the polymer material which constitute the composite piezoelectric layer. For example, if the acoustic impedance of the piezoelectric material is 30 MR and the acoustic impedance of the polymer material is 1.5 MR, the acoustic impedance of the composite piezoelectric layer={the volume of the piezoelectric material×30+the volume of the polymer material×1.5}/the volume of the composite piezoelectric material     (1)

Figure 3A:
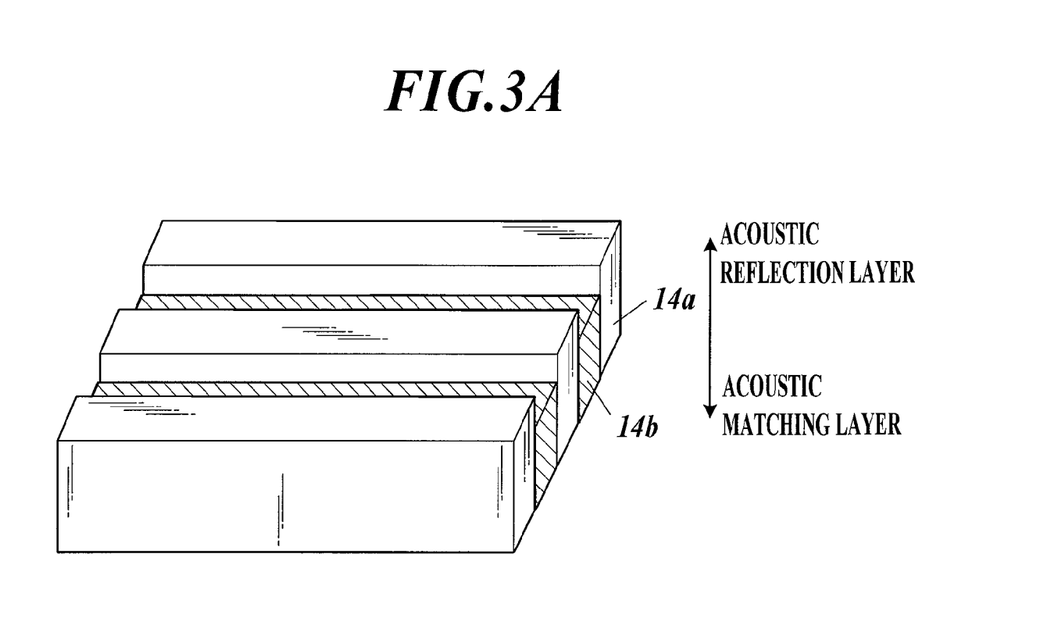
FIG. 3A shows an outline of a composite piezoelectric layer.
Figure 3B:
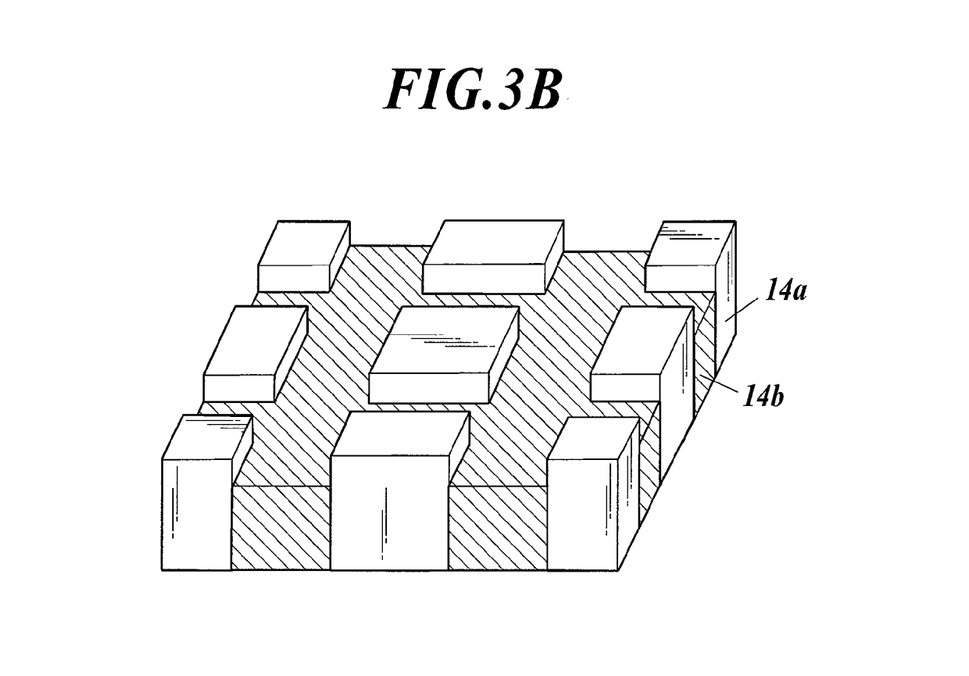
FIG. 3B shows another example of an outline of the composite piezoelectric layer.

With reference to FIGS. 3A and 3B, the composite piezoelectric layer 14 according to the embodiment will be described below.

FIG. 3A shows an outline of a composite piezoelectric layer which is an enlarged view of the composite piezoelectric layer 14 shown in FIG. 2B. A one-dimensional array composite piezoelectric layer 14 is formed by arranging the piezoelectric material 14a and the polymer material 14b alternately in one direction and integrating them as shown in FIG. 3A. A two-dimensional array composite piezoelectric layer 14 as shown in FIG. 3B can also be used. The composite piezoelectric layer 14 according to the present invention is not limited to the above described composite piezoelectric layers 14, and it is sufficient that the composite piezoelectric layer 14 according to the present invention has the configuration where the polymer material 14 is concaved inside than the piezoelectric material 14a with respect to the direction toward the acoustic reflection layer 13.

In the above, an example where a piezoelectric material and a polymer material are arranged in a one-dimensional matrix array or in a two-dimensional matrix array is described as a composite piezoelectric material. However, "two-dimensional array" in the present invention also includes two-dimensional arrays other than linear arrangement such as in a case where a piezoelectric material and a polymer material are arranged alternately and concentrically.

Next, a manufacturing method of the ultrasound probe 1 including the above described composite piezoelectric layer 14 will be described below with reference to FIG. 4. Here, for convenience, a description will be given for a manufacturing method of an ultrasound probe provided with a one-dimensional array composite piezoelectric layer.

Figure 4:
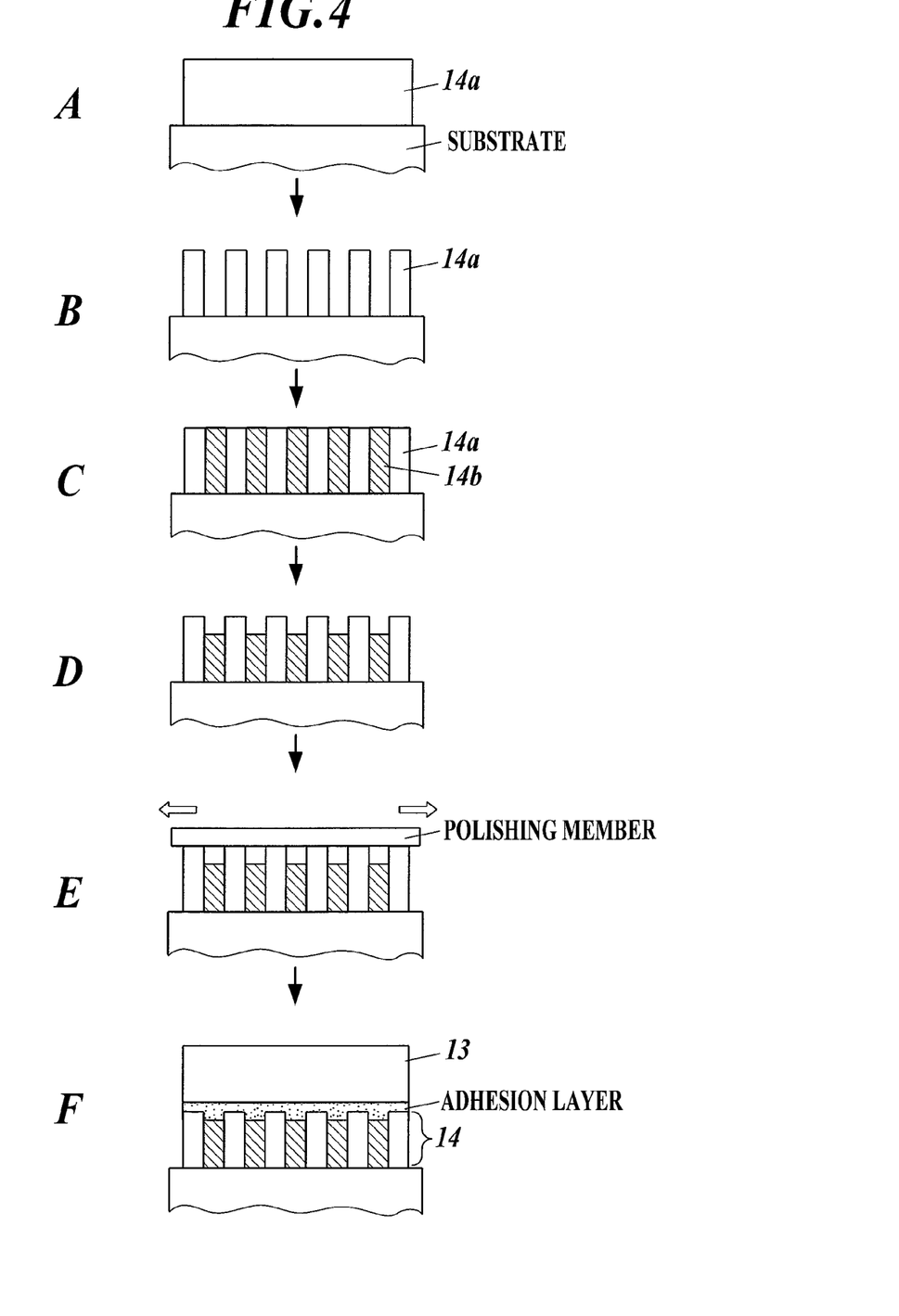
FIG. 4 shows a flow of a manufacturing method of the ultrasound probe.

In the first step, in order to arrange the piezoelectric material 14a and the polymer material 14b on a substrate in a one-dimensional array, spaces for filling the polymer material 14b are formed by removing the piezoelectric material with predetermined intervals therebetween by etching or dicing (B in FIG. 4). Thereafter, by filling the spaces with the polymer material 14b (C in FIG. 4), a composite piezoelectric layer in which the polymer material 14b and the piezoelectric material 14a are arranged alternately in a one-dimensional array and integrated is formed.

In the above described step, it is sufficient that the piezoelectric material 14a and the polymer material 14b are arranged in a one-dimensional array, and for example, the polymer material 14b and the piezoelectric material 14a may be arranged on a substrate in a one-dimensional array by first arranging the piezoelectric material 14a on the substrate with predetermined intervals therebetween and then filling the spaces with the polymer material 14b without using the etching method or the dicing method.

In the second step (a polymer material removing step), by removing parts of the polymer material 14b among the piezoelectric material 14a and the polymer material 14b arranged on the substrate in a one-dimensional array by etching or dicing, a composite piezoelectric layer in which the side of the polymer material opposite to the side facing the substrate is concaved comparing to the side of the piezoelectric material opposite to the side facing the substrate can be formed (D in FIG. 4). That is, parts of the polymer material are removed so that the bonding surface of the composite piezoelectric layer that bonds with the aftermentioned acoustic reflection layer by an adhesion layer be a bonding surface where the polymer material is concaved in the direction opposite toward the acoustic reflection layer side, which is to be bonded, comparing to the piezoelectric material. The etching and dicing will be described later.

In the third step (a polishing and smoothing step), mirror polishing is performed on the bonding surface of the piezoelectric material 14a which is the surface opposite to the surface of the piezoelectric material 14a that contacts with the substrate to smoothen each part of the bonding surface formed of the piezoelectric material (E in FIG. 4). Because a composite piezoelectric layer in which the side of the polymer material opposite to the side facing the substrate is concaved comparing to the side of the piezoelectric material that is opposite to the side facing the substrate is formed in the second step, mirror polishing can be performed only on the bonding surfaces of the piezoelectric material 14a which are the surfaces opposite to the surface that contacts with the substrate, and the bonding surfaces can be smoothened.

In a viewpoint of being able to be used in a wider frequency band by making the adhesion layer thin, it is preferred that the surface roughness Ra (μm) of the parts formed of piezoelectric material is Ra≤0.4, although depends on the hardness of the piezoelectric material and the acoustic reflection layer to be bonded.

By performing polishing to smoothen the bonding surfaces of the piezoelectric material 14a which are the surfaces opposite to the surfaces that contact with the substrate in the bonding surface of the composite piezoelectric layer, there is a possibility that the piezoelectric material 14a be at the same level as the bonding surfaces of the polymer material by being shaved off. Therefore, for example, in a case where polishing is performed on the bonding surfaces of the piezoelectric material 14a which are the surfaces opposite to the surfaces that contact with the substrate so that the surface roughness thereof be 0.4 μm or smaller, in order to prevent the piezoelectric material and the polymer material being polished at the same time as described above, it is preferred that the polymer material is concaved inside for 2.0 μm or more with respect to the acoustic reflection layer.

On the other hand, in a view point that the after-mentioned electrode layer will be difficult to form and in a view point of durability of the composite piezoelectric layer, it is preferred that the polymer material does not be concaved inside with respect to the acoustic reflection layer to the extent that the height of the polymer material is 50% or less than the height of the piezoelectric material.

In the fourth step (a bonding step), an adhesion layer is applied to the above mentioned bonding surfaces on which polishing is performed and the bonding surfaces of the composite piezoelectric layer 14 where the acoustic reflection layer is to be bonded and the bonding surface of the acoustic reflection layer 13 are bonded (F in FIG. 4). In order to bond the bonding surfaces of the piezoelectric parts of the composite piezoelectric layer and the bonding surface of the acoustic reflection layer, an adhesion layer is required. However, in a viewpoint of realizing wider bandwidth, it is preferred that the adhesion layer between the bonding surfaces of the piezoelectric parts of the composite piezoelectric layer and the bonding surface of the acoustic reflection layer be thin. For example, in a case to be used in a center frequency band 7 MNz or wider, it is preferred to adjust so that the thickness t (μm) of the adhesion layer at the above parts be $0 < t \leq 1.0$.

When forming the above described adhesion layer, the concaves at the polymer material parts generated by the polymer material being removed in the second step (the polymer removing step) are filled with the adhesion layer.

By the etching, desired parts (the polymer material 14b parts) can be removed by performing etching with plasma or gas after covering the parts not to be removed by the etching (the piezoelectric material 14a parts) with an etching mask.

As for such etching mask, a mask having lower etching rate than the piezoelectric material is used. For example, $SiO_2$, $Si_3N_4$ and calcium fluoride films which are formed by CVD and nickel and copper by electroplating may be used. In addition, plastic resist may be used as-is.

On the other hand, dicing is used to form spaces, in which the polymer material 14b is to be filled, by forming grooves having depth reaching the substrate in the piezoelectric material placed on the substrate by dicing saw or to remove parts of the polymer material by shaving the material using a dicing saw and forming the composite piezoelectric layer in which the polymer material is concaved comparing to the piezoelectric material with respect to the acoustic reflection layer. As for the dicing saw, those configured of diamond wheel or the like may be used. Hereinafter, a method to shave the polymer material 14b by etching will be described.

Etching according to the embodiment may be performed by masking the piezoelectric material parts with the above mentioned etching mask; however, etching may also be performed on the desired parts by utilizing the difference in etching rate between the piezoelectric material 14a and the polymer material 14b, for example.

Comparing to the material used for the polymer material 14b, etching speed of the piezoelectric material 14a is extremely slow. Thus, by using the difference in etching durability between the piezoelectric material 14a and the polymer material 14b, the materials can be shaved so that the polymer material 14b will be more inside since the polymer material 14b is etched and removed faster than the piezoelectric material 14a.

After the composite piezoelectric layer is formed by the above described manufacturing method, concaves are formed by removing parts of the polymer material 14b by etching, etc. However, concaves may be formed when forming the composite piezoelectric layer, that is, when filling the polymer material 14b in the spaces in the piezoelectric material while adjusting the amount of the polymer material 14b to be filled so that the surfaces of the polymer material opposite to the surfaces that contact with the substrate be concaved comparing to the surfaces of the piezoelectric material opposite to the surfaces that contact with the substrate. In such case, the above described polymer removing step can be omitted.

As for the piezoelectric material 14a, piezoceramics such as ceramics of lead zirconate titanate (PZT), relaxor system, lead niobate system, lead titanate system, etc. and single crystals such as lead zinc niobate titanate (PZNT), lead magnesium niobate lead titanate (PMNT), etc. are preferably used.

As for the polymer material 14b, organic synthetic polymer materials such as epoxy resin, silicone resin, urethane resin, polyethylene resin, polyurethane resin, etc. may be used. Natural organic polymer materials such as natural rubber may also be used. Since these organic polymer materials have larger specific heat and smaller heat conductivity comparing to the above described piezoelectric material, damages due to heat such as frictional heat generated when performing dicing in the first step can be prevented. For example, epoxy resin has heat conductivity about 0.2 W/(m·K) and is advantageous in terms of specific heat and heat conductivity. Further, these organic polymer materials can prevent physical damages on the piezoelectric material at the time of cutting process.

A hard resin having a predetermined hardness in order to improve accuracy in the cutting work when performing dicing is preferred to be applied as the organic polymer material used in the embodiment. In particular, a hard resin having the Rockwell hardness of 80 or more is preferred, for example. Further, in order to improve the element characteristics after arraying, it is preferred that the polymer material has the speed of sound 1 km/s or faster. In the embodiment, epoxy resin whose speed of sound is 2 km/s or faster and Rockwell hardness is M80 or more is used. Here, an inorganic polymer material may also be used instead of an organic polymer material.

Figure 5:
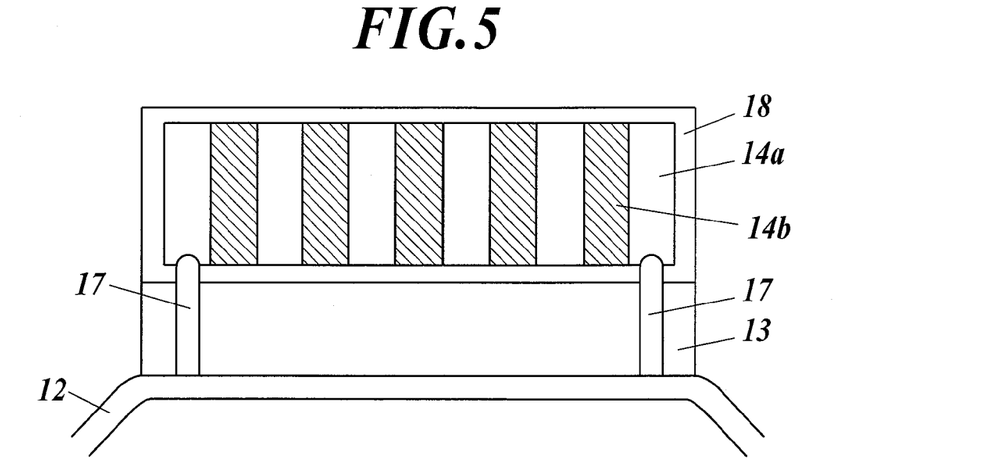
FIG. 5 shows rough positions of an electrode layer and a flexible printed board.

Next, the electrode layer 18 and the flexible printed board will be described with reference to FIG. 5.

The electrode layer 18 is provided on the entire surface where the composite piezoelectric layer 14 is formed. The electrode layer 18 applies power voltage from the signal lead-out flexible printed board (FPC) to the composite piezoelectric layer 14. When manufacturing the ultrasound probe according to the present invention, the electrode layer is preferably formed after the third step which is the polishing process. Hereinafter, a method for making the flexible printed board and the composite piezoelectric layer electrically conductive after the third step will be described.

After the third step, the electrode layer is formed on the entire surface of the composite piezoelectric layer by spattering or the like. Thereafter, the acoustic reflection layer and the composite piezoelectric layer where the electrode layer is formed on the surface thereof are bonded by the adhesion layer. After the bonding, the electrode layer on the acoustic reflection layer side of the composite piezoelectric layer is shaved off by dicing in the direction toward the acoustic reflection layer side surface of the composite piezoelectric layer from the side of the acoustic reflection layer opposite to the side facing the composite piezoelectric layer, the shaving being performed to the insulating position. The insulators 17 are formed by filling the cut out holes formed by dicing with an adhesive. By forming the insulators 17, the center part of the electrode layer 18 separated by the insulators 17 is made conductive with the composite piezoelectric material and the ground electrode layer of the flexible printed board through the conductive acoustic reflection layer as shown in FIG. 5. On the other hand, the two end parts of the electrode layer 18 separated by the insulators 17 are made conductive with the flexible printed board.

Here, in the above procedure, the step of shaving off the desired parts in the electrode layer which is formed on the entire surface of the composite piezoelectric layer to obtain isolation is performed after the acoustic reflection layer and the composite piezoelectric layer are bonded. However, this step may be performed before the bonding. In such case, cut out holes are formed by cutting out the acoustic reflection layer at places matching the insulation parts in the electrode layer which is formed on the surface of the composite piezoelectric layer by dicing before the bonding and the cut out holes are filled with an adhesive.

Materials such as gold (Au), platinum (Pt), silver (Ag), palladium (Pd), copper (Cu), aluminum (Al), nickel (Ni), tin (Sn), etc. are suggested to be used for the electrode layer 18. The electrode layer 21 and the shared electrode layer 22 are formed by first, forming the base metal such as titanium (Ti), chromium (Cr) or the like in the thickness of 0.002 to 1.0 μm by spattering and then, forming a metallic material formed of a metal based on the above metallic elements and alloys thereof, further a part of insulation material as needed, in the thickness of 0.02 to 10 μm by spattering, deposition or other suited method. Such forming of the electrode layer may be performed by screen printing, dipping or thermal spraying using conductive paste which is a combination of minute metal powder and low melting glass other than spattering.

The acoustic reflection layer 13 is a reflection layer for reflecting the ultrasound generated in the composite piezoelectric layer 14. The acoustic reflection layer 13 is bonded with the surface of the composite piezoelectric layer 14 opposite to the surface facing a subject, and the bonding surface of the acoustic reflection layer 13 opposite to the bonding surface with the composite piezoelectric layer 14 is bonded with the backing layer 11. The acoustic reflection layer 13 reflects the ultrasound of the composite piezoelectric layer 14 emitted toward the direction opposite to the direction toward a subject toward the subject to increase the power of the ultrasound entering the subject.

Since the acoustic reflection layer 13 is used for reflecting the ultrasound, it is sufficient that the acoustic impedance of the acoustic reflection layer is relatively higher than the acoustic impedance of the composite piezoelectric layer calculated by the above expression (1). As for the acoustic reflection layer, tungsten or the like can be used.

The acoustic reflection layer 13 is also a substance having high conductivity and electrically connects the after-mentioned flexible printed board 12 and the composite piezoelectric layer 14. The acoustic reflection layer 13 is electrically insulated by having the cut out holes matching the insulation parts in the electrode layer 18 of the composite piezoelectric layer 14.

The backing layer 11 supports the acoustic reflection layer 13, the composite piezoelectric layer 14 and the acoustic matching layer 15 and is configured of an ultrasound absorber which may absorb unneeded ultrasound. The backing layer 11 is attached on the board surface of the composite piezoelectric layer 14 opposite to the direction in which the composite piezoelectric layer 14 transmits and receives the ultrasound to and from a subject, and the backing layer 11 absorbs the ultrasound which transmitted through the acoustic reflection layer among the ultrasound generated toward the direction opposite to the direction toward a subject.

As for the backing material forming the backing layer 11, a rubber composite or an epoxy resin composite which is formed by press molding natural rubber, ferrite rubber, epoxy resin or a combination of these materials and thermoplastic resins such as tungsten oxide, titanium oxide, ferrite, vinyl chloride, polyvinyl butylal (PVB), ABS resin, polyurethane (PUR), polyvinyl alcohol (PVAL), polyethylene (PE), polypropylene (PP), polyacetal (POM), polyethylene terephthalate (PETP), fluororesin (PTFE) polyethylene glycol, polyethylene terephthalate-polyethylene glycol copolymer, etc. can be applied.

The backing material is preferably configured of a blended material of a rubber composite and an epoxy resin composite. The shape of the backing layer may be selected arbitrarily according to the shape of the composite piezoelectric layer 14 or the shape of the ultrasound probe 1 including the composite piezoelectric layer 14.

The acoustic matching layer 15 matches the acoustic impedance between the composite piezoelectric layer 14 and a subject to prevent reflection at the interface. The acoustic matching layer 15 is attached, on the side of the composite piezoelectric layer 14 opposite to the side toward the subject in the direction transmission and reception of ultrasound is performed. The acoustic matching layer 15 has an intermediate acoustic impedance of the composite piezoelectric layer 14 and a subject.

The acoustic matching layer 15 may be a single layer or may be formed of a plurality of layers, preferably having two layers or more, and more preferably having four layers or more. The layer thickness of the acoustic matching layer 15 is preferably set so that the wavelength of ultrasound be $\lambda/4$ when the wavelength is $\lambda$. If the layer thickness of the acoustic matching layer 15 is not set appropriately, there is a possibility that a plurality of unnecessary spurious appear at the frequency point different from the original resonance frequency and that the basic acoustic characteristic changes drastically. As a result, the reverberation time may increase and sensitivity and S/N may be degraded due to distortion in the waveform of the reflection echo. Normally, the thickness of such acoustic matching layer 15 is within the range of about 200 to 500 μm.

As for the material used for the acoustic matching layer 15, aluminum, aluminum alloy (for example, AL-Mg alloy), magnesium alloy, macor glass, glass, fused quartz, copper graphite, PE (polyethylene), PP (polypropylene), PC (polycarbonate), ABC resin, ABS resin, AAS resin, AES resin, nylon (PA6, PA6-6), PPO (polyphenylene oxide), PPS (polyphenylene sulfide: can include glass fiber), PPE (polyphenylene ether), PEEK (polyethertherketone), PAI (polyamide imide), PETP (polyethylene terephthalate), epoxy resin, urethane resin, etc. can be used. Preferably, materials where zinc oxide, titanium oxide, silica, alumina, red iron oxide, ferrite, tungsten oxide, yttrium oxide, barium sulfate, tungsten, molybdenum, etc. are added as fillers in thermosetting resin such as epoxy resin and molded can be used.

According to the embodiment, broad band ultrasound can be emitted to a subject since the adhesion layer between the piezoelectric parts of the composite piezoelectric layer and the acoustic reflection material can be thin and the bonding surface of the composite piezoelectric layer bonding with the acoustic reflection layer is also a surface where the piezoelectric material and the polymer material are alternately arranged. Therefore, an ultrasound probe provided with a composite piezoelectric layer where its durability and stability are improved can be provided.

Next, the ultrasound diagnostic imaging apparatus 2 will be described with reference to the drawings.

Figure 6:
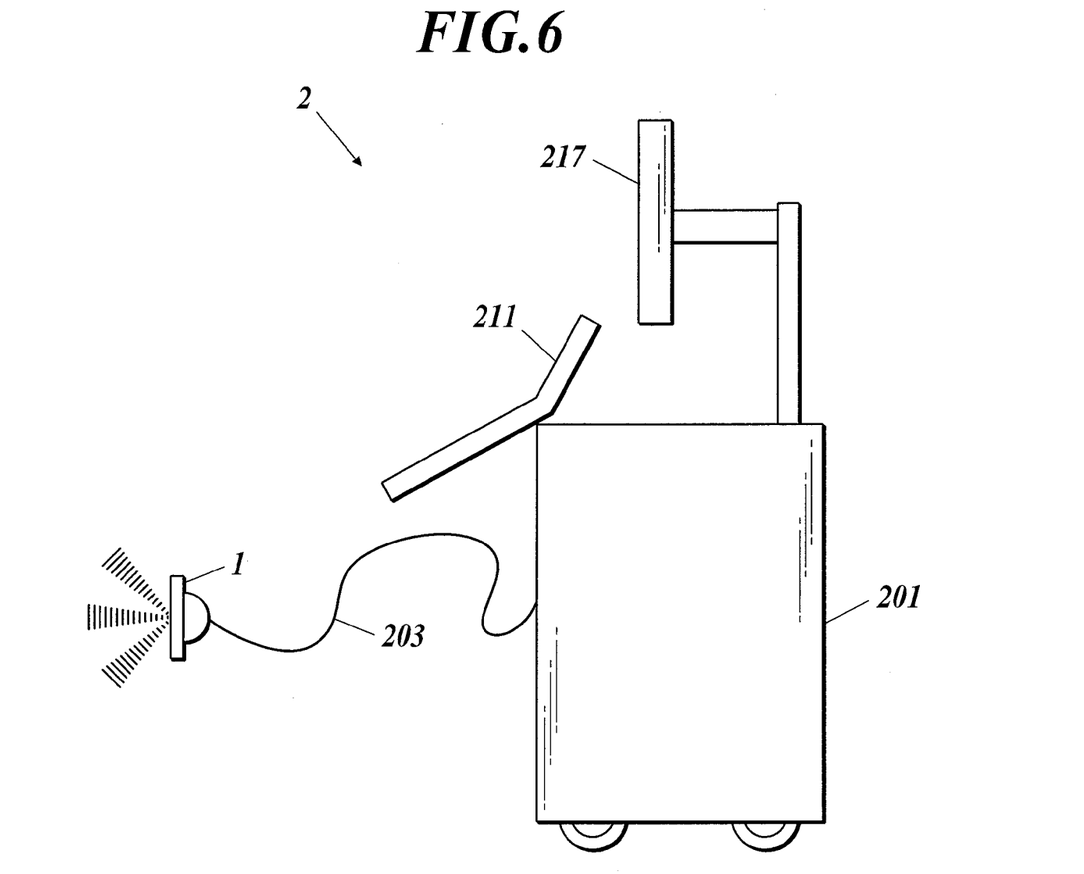
FIG. 6 shows an outer configuration of an ultrasound diagnostic imaging apparatus.

FIG. 6 is a side view showing an outline configuration of the ultrasound diagnostic imaging apparatus 2 according to the embodiment.

The ultrasound diagnostic imaging apparatus 2 according to the embodiment includes the ultrasound diagnostic imaging apparatus main body 201 and the ultrasound probe 1. The ultrasound probe 1 transmits ultrasound (transmission ultrasound) to a subject such as a living body (not shown) and receives the reflected wave (reflected ultrasound: echo) of the ultrasound reflected off the subject. The ultrasound diagnostic imaging apparatus main body 201 is connected with the ultrasound probe 1 via the cable 203. The ultrasound diagnostic imaging apparatus main body 201 transmits a drive signal which is an electric signal to the ultrasound probe 1 to make the ultrasound probe 1 transmit the transmission ultrasound to the subject and the ultrasound diagnostic imaging apparatus main body 201 creates an ultrasound image of the internal condition of the subject on the basis of the received signal which is an electric signal generated by the ultrasound probe 1 according to the reflected ultrasound from inside of the subject received by the ultrasound probe 1.

Figure 7:
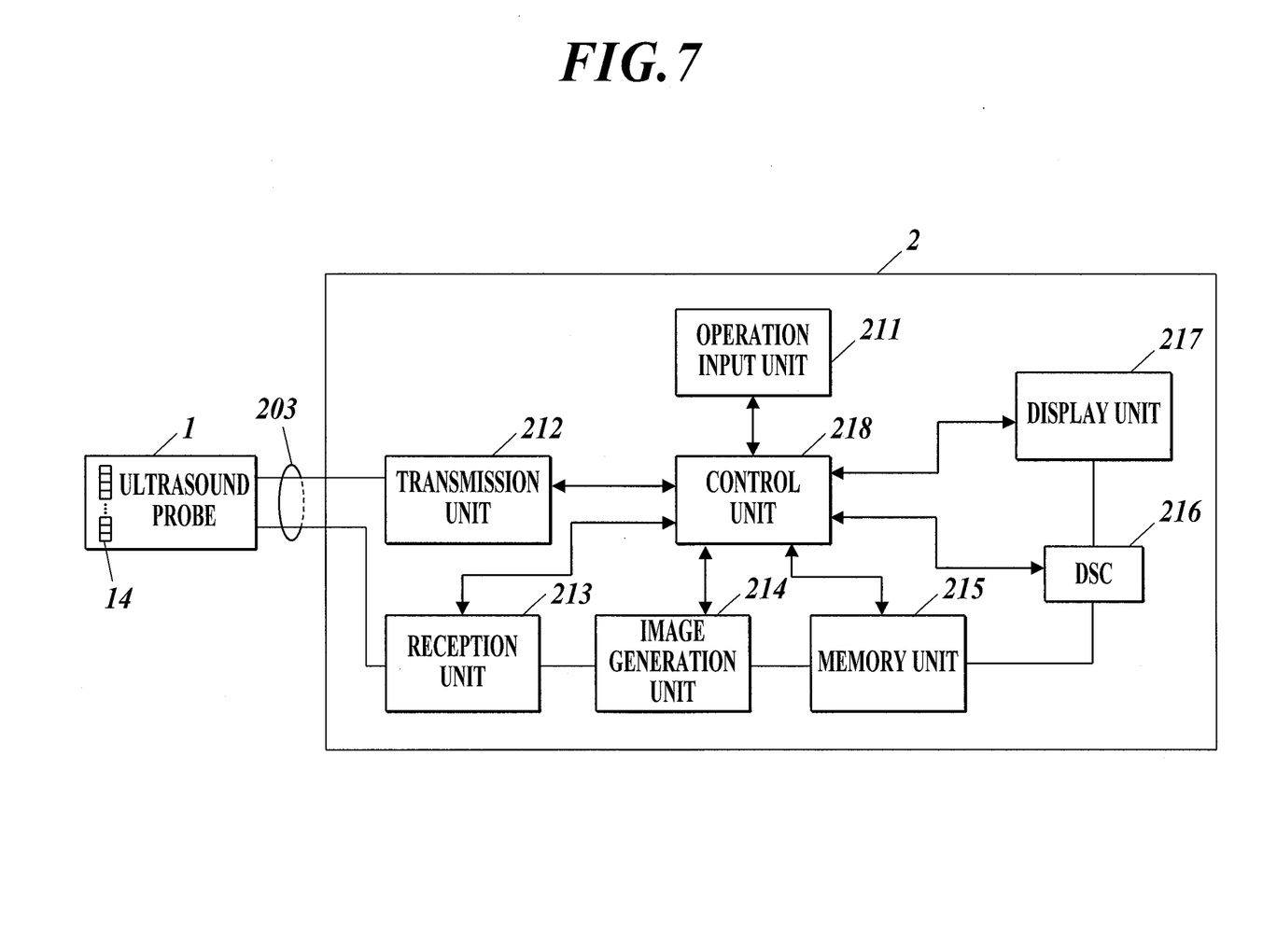
FIG. 7 is a block diagram showing an outline configuration of the ultrasound diagnostic imaging apparatus.

As shown in FIG. 7, the ultrasound diagnostic imaging apparatus main body 201 includes an operation input unit 211, a transmission unit 212, a reception unit 213, an image generation unit 214, a memory unit 215, a DSC (Digital Scan Converter) 216, a, display unit 217 and a control unit 218, for example.

The operation input unit 211 includes various types of switches, buttons, a track ball, a mouse, a key board and the like for inputting commands for instructing the start of diagnosis and data such as personal information relating to a subject, etc. and the operation input unit 211 outputs operations signals to the control unit 218.

Figure 8:
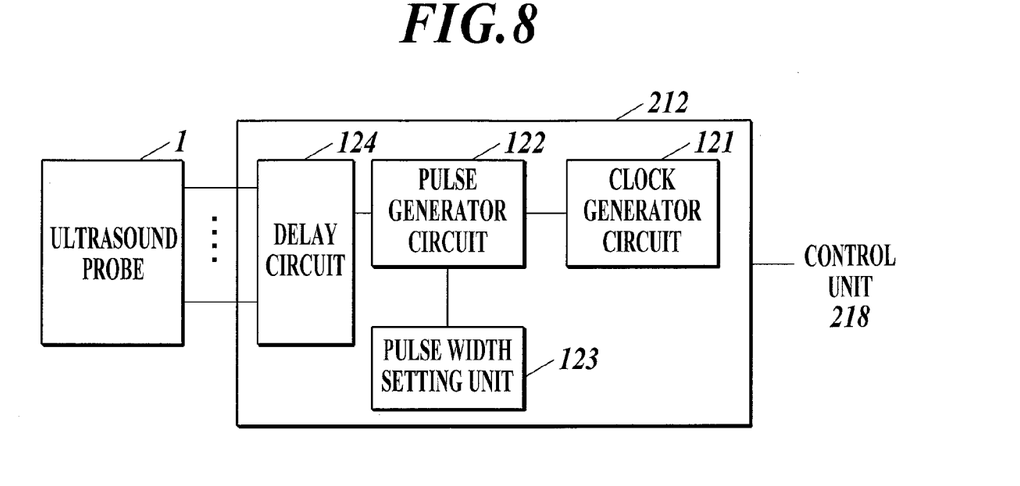
FIG. 8 is a block diagram showing an outline configuration of a transmission unit.

The transmission unit 212 is a circuit for supplying a drive signal which is an electric signal to the ultrasound probe 1 via the cable 203 according to the control of the control unit 218 to make the ultrasound probe 1 generate transmission ultrasound. More specifically, as shown in FIG. 8, the transmission unit 212 includes a clock generator circuit 121, a pulse generator circuit 122, a pulse width setting unit 123 and a delay circuit 124, for example.

The clock generator circuit 121 is a circuit for generating a clock signal for deciding the transmission timing the transmission frequency of a drive signal.

Figure 9:
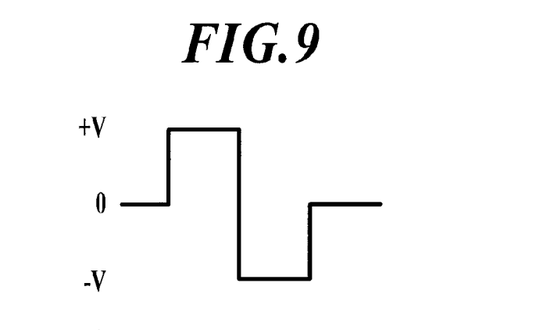
FIG. 9 is an explanatory diagram of a drive waveform of a pulse signal.

The pulse generator circuit 122 is a circuit for generating a pulse signal as a drive signal in a predetermined cycle. As shown in FIG. 9, the pulse generator circuit 122 can generate a pulse signal of rectangular wave by switching and outputting a three-valued voltage, for example. At this time, the amplitude of the pulse signal is set so that the amplitude in positive polarity and the amplitude in negative polarity be the same; however, this is not limitative in any way. The pulse generator circuit' 121 may generate a pulse signal by switching a two-valued voltage.

The pulse width setting unit 123 sets the pulse width of a pulse signal which is output from the pulse generator circuit 122. That is, the pulse generator circuit 122 outputs a pulse signal of a pulse waveform according to the pulse width set by the pulse width setting unit 123. Pulse width can vary by input operations through the operation input unit 211, for example. Further, the configuration may be such that by discriminating the ultrasound probe 1 which is connected to the ultrasound diagnostic imaging apparatus main body 201, the pulse width corresponding to the discriminated ultrasound probe 1 is to be set.

As shown in FIG. 7, the reception unit 213 is a circuit for receiving a received signal which is an electric signal from the ultrasound probe 1 via the cable 203 according to the control of the control unit 218. The reception unit 213 includes an amplifier, an A/D converter circuit and a phasing addition circuit, for example. The amplifier is a circuit for amplifying the received signal at a predetermined amplification factor which is preset in each path corresponding to each element, each part whose two ends are bounded by the insulators 17 of the composite piezoelectric layer being one elements (shown in FIG. 2). The A/D converter circuit is a circuit for performing analog-digital conversion (A/D conversion) of the amplified received signal. The phasing addition circuit is a circuit for matching the time phase by applying delay time to the A/D converted received signal for each path corresponding to each element of the composite piezoelectric layer and generating sound ray data by adding (phasing addition).

The image generation unit 214 performs envelope detection and logarithm amplification on the sound ray data received from the reception unit 213 and generates image data by performing brightness conversion by adjusting the gain and the like. That is, image expresses the intensity of the received signal in brightness. The image data generated in the image generation unit 214 is transmitted to the memory unit 215.

The memory unit 215 is configured of a semiconductor memory such as a DRAM (Dynamic Random Access Memory), for example, and the image data transmitted from the image generation unit 214 is stored in frame units. That is, the memory unit 215 may store the image data as ultrasound diagnostic image data configured of frame units. The ultrasound diagnostic image data stored in the memory unit 215 is read according to the control of the control unit 218 and is transmitted to the DSC 216.

The DSC 216 converts the ultrasound diagnostic image data received from the memory unit 215 into image signal of television signal scanning mode and outputs the image signal to the display unit 217.

As for the display unit 217, display devices such as a LCD (Liquid Crystal Display), a CRT (Cathode-Ray Tube) display, an organic EL (Electronic Luminescence) display, an inorganic EL display and a plasma display can be used. The display unit 217 performs displaying of the ultrasound diagnostic image on the display screen according to the image signal output from the DSC 216. Here, a printing device such as a printer or the like may be used instead of a display device.

The control unit 218 includes a CPU (Central Processing Unit), a ROM (Read Only Memory) and a. RAM (Random Access Memory), for example. The control unit 218 reads and opens various processing programs such as a system program stored in the ROM in the RAM and integrally controls the operation of the parts in the ultrasound diagnostic imaging apparatus 2 according to the opened program.

The ROM is configured of a non-volatile memory of a semiconductor or the like, and the system program corresponding to the ultrasound diagnostic imaging apparatus 2, various processing programs which can be executed on the system program, various data, etc. are stored in the ROM. These programs are stored in a program code format which a computer can read, and the CPU sequentially executes operations according to the program code.

The RAM forms a work area for temporarily storing various programs which are to be executed by the CPU and data according to these programs.

The form of a drive signal is not specifically limited and can be selected arbitrarily from a sine wave, a cosine wave, a rectangular wave, etc. Further, a signal formed by synthesizing a plurality of the above signals. In a view point of forming a simple and small circuit, it is preferred that a drive signal is a rectangular wave including a plurality of pulses. At this time, at least one of the plurality of pulses preferably has a pulse width (duty) different from other pulses. Thereby, since the frequency band width of the drive signal be wide, the frequency band width of the ultrasound to be transmitted can be even wider and the time resolution, that is, the distance resolution in the depth direction can be improved more.

Figure 10:
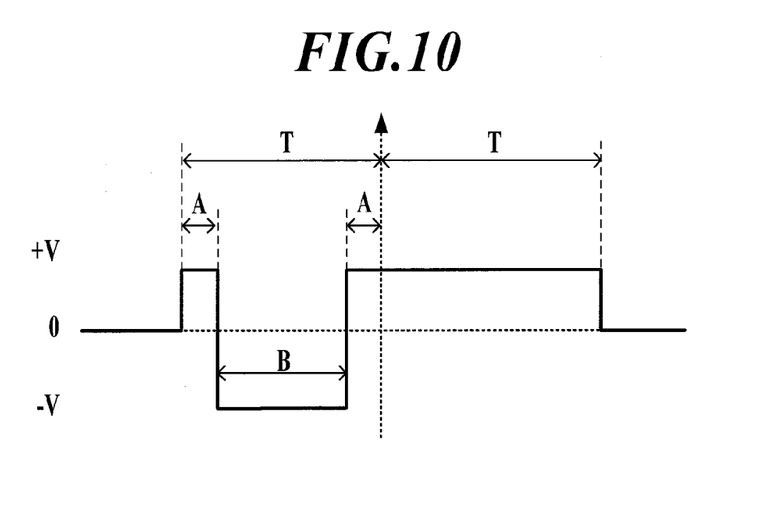
FIG. 10 is an explanatory diagram of a waveform of a pulse signal which is to be transmitted.

FIG. 10 shows an example of the shape of such drive signal. The drive signal shown in FIG. 10 is a square wave including the first pulse signal (pulse signal A), the second pulse signal having different polarity from the first pulse signal (pulse width B) and the third pulse signal having the same polarity as the first pulse signal (pulse width A). The transmitted pulse signal is set so that its cycle is 2T, and the pulse widths of the first pulse signal, the second pulse signal and the third pulse signal should be set individually so as to fulfill T=2A+B. Thereby, a pulse signal can be designed easily by synthesizing the first and the third pulse signals having the same polarity and the second pulse signal having the different polarity. Further, the exemplified square wave is a drive signal where the pulse widths of the first pulse signal and the third pulse signal are the same. However, if the pulse widths of the first pulse signal, the second pulse signal and the third pulse signal are set respectively to 16 ns, 56 ns and 104 ns, the pulse widths of the first pulse to the third pulse can be different from one another. By changing the pulse widths as described above, the peak position indicating the frequency response characteristics of the ultrasound probe can be changed to a desired frequency band and the frequency band width of the drive signal can be even wider.

By providing the above described ultrasound diagnostic apparatus with the ultrasound probe 1, an ultrasound diagnostic apparatus which can emit broad band ultrasound to a subject and which provides a high resolution ultrasound image can be provided.

The entire disclosure of Japanese Patent Application No. 2013-016800 filed on Jan. 31, 2013 is incorporated herein by reference in its entirety.

What is claimed is:

1. An ultrasound probe which outputs ultrasound on a basis of a drive signal which is to be received, the probe comprising:
    a composite piezoelectric layer in which a piezoelectric material and a polymer material are arranged in a one-dimensional array or in a two-dimensional array so that an upper edge surface of the piezoelectric material and an upper edge surface of the polymer material are arranged alternately;
    an acoustic reflection layer which has an acoustic impedance higher than an acoustic impedance of the composite piezoelectric layer; and
    an adhesion layer which bonds the acoustic reflection layer on the composite piezoelectric layer,
    wherein the upper edge surface of the piezoelectric material and the upper edge surface of the polymer material are on a bonding surface side of the composite piezoelectric layer which is bonded to the acoustic reflection layer, and the upper edge surface of the polymer material is concaved in a direction opposite to the bonding surface side as compared to the upper edge surface of the piezoelectric material.

2. The ultrasound probe of claim 1, wherein a thickness t (μm) of the adhesion layer between the upper edge surface of the piezoelectric material of the composite piezoelectric layer and the acoustic reflection layer is 0 μm<t<1.0 μm.

3. The ultrasound probe of claim 1, wherein a surface roughness Ra (μm) of a surface of the piezoelectric material in the composite piezoelectric layer opposite to the bonding surface side is Ra≤0.4 μm.

4. An ultrasound diagnostic imaging apparatus, comprising:
    the ultrasound probe of claim 1;
    a transmission circuit which generates the drive signal; and
    a processor which performs control to generate ultrasound image data for displaying an ultrasound image on a basis of the received signal output by the ultrasound probe.

5. The ultrasound diagnostic imaging apparatus of claim 4, wherein the drive signal is a rectangular wave including a plurality of pulses, a pulse width of at least one pulse among the plurality of pules being different from pulse widths of other pulses.

6. The ultrasound diagnostic imaging apparatus of claim 4, wherein:
    the drive signal includes a first pulse signal, a second pulse signal whose polarity is different from the first pulse signal and a third pulse signal whose polarity is the same as the first pulse signal, and
    a pulse width of the first pulse signal, the pulse width of the second pulse signal, and the pulse width of the third pulse signal are different from one another.

7. A manufacturing method for manufacturing the ultrasound probe according to claim 1, the manufacturing method comprising:
    forming the composite piezoelectric layer in which the piezoelectric material and the polymer material are arranged alternately;
    removing parts of the polymer material on the bonding surface side of the composite piezoelectric layer which bonds with the acoustic reflection layer so that the upper edge surface of the polymer material is concaved in the direction opposite to the bonding surface side as compared to the upper edge surface of the piezoelectric material;
    polishing a bonding surface of the composite piezoelectric layer after the removing; and
    bonding of the bonding surface of the composite piezoelectric layer and the acoustic reflection layer by the adhesion layer.

8. The manufacturing method of an ultrasound probe of claim 7, wherein removing of the parts of the polymer material in the removing is performed by etching.

9. The manufacturing method of an ultrasound probe of claim 7, wherein removing of the parts of the polymer material in the removing is performed by dicing.

10. A manufacturing method for manufacturing the ultrasound probe according to claim 1, the manufacturing method comprising:
    filling the polymer material in spaces formed in the piezoelectric material with a predetermined interval therebetween to form the composite piezoelectric layer;
    polishing a bonding surface of the composite piezoelectric layer after the filling; and bonding of the bonding surface of the composite piezoelectric layer and the acoustic reflection layer by the adhesion layer, wherein in the filling, the polymer material is filled so that the upper edge surface of the polymer material is concaved in the direction opposite to the bonding surface side as compared to the upper edge surface of the piezoelectric material.

11. The ultrasound probe of claim 1, wherein the piezoelectric material is not formed on the polymer material in the composite piezoelectric layer in a direction toward the bonding surface side of the composite piezoelectric layer which is bonded with the acoustic reflection layer.

12. The ultrasound probe of claim 1, wherein the composite piezoelectric layer includes an electrode layer on a surface on the bonding surface side.

* * * * *